United States Patent [19]
Stern et al.

[11] Patent Number: 5,827,721
[45] Date of Patent: Oct. 27, 1998

[54] BH55 HYALURONIDASE

[75] Inventors: Robert Stern; Gregory I. Frost; Jackson Hall; Svetlana Shuster, all of San Francisco; Gail T. Colbern, Pacifica; Bent Formby, Santa Barbara, all of Calif.

[73] Assignee: The Regents of the University of California, Oakland, Calif.

[21] Appl. No.: 919,089

[22] Filed: Aug. 27, 1997

Related U.S. Application Data

[62] Division of Ser. No. 419,594, Apr. 7, 1995, Pat. No. 5,747,027.

[51] Int. Cl.$^6$ .............................. C12N 9/26; C12N 15/00; C12N 5/00; C07H 21/04
[52] U.S. Cl. ................... 435/201; 435/320.1; 435/252.3; 435/254.11; 435/325; 536/23.2
[58] Field of Search ................................ 435/201, 320.1, 435/252.3, 254.11, 325; 536/23.2

[56] References Cited

U.S. PATENT DOCUMENTS

| | | | |
|---|---|---|---|
| 4,179,337 | 12/1979 | Davis et al. | 435/181 |
| 4,800,159 | 1/1989 | Mullis et al. | 435/172.3 |
| 4,820,516 | 4/1989 | Sawyer et al. | 424/94.62 |
| 5,166,322 | 11/1992 | Shaw et al. | 530/351 |
| 5,206,344 | 4/1993 | Katre et al. | 530/351 |

FOREIGN PATENT DOCUMENTS

WO 88/02261   4/1988   WIPO .

OTHER PUBLICATIONS

Dorfman et al., "A turbidimetric method for the assay of hyaluronidase," 1948, *J. Biol. Chem.* 172:367–375.
Reissig et al., "A modified colorimetric method for the estimation of N–acetylamino sugars," 1955 *J. Biol. Chem.* 217:959–966.
Ozello et al., "Growth–promoting activity of acid mucopolysaccharides on a strain of human mammary carcinoma cells," 1960 *Cancer Res.* 20:600–604.
Takeuchi et al., "Variation in glycosaminoglycan components of breast tumors," 1976 *Cancer Res.* 36:2133–2139.
Pawlowski et al., "The effects of hyalurodinase upon tumor formation in Balb c Mice Painted with 7.12–Dimethylbenz–(α)Anthracene,," 1979, *Int. J. Cancer* 23;105–109; Abstract 415, (1981) *Proceedings* 22:105.
Tengblad, "Affinity Chromatography on immmobilized hyaluronate and its application to the isolation of hyaluronate binding proteins from cartilage," 1979, *Biochim. Biophys. Acta* 578:281–289.
Kimata et al., "Increased Synthesis of Hyaluronic Acid by Mouse Mammary Carcinoma Cell Variants with High Metastic Potential", 1983, *Cancer Res.* 43:1347–1354.
Doctor et al., "Isolation and Properties of a New Anticoagulant Protein From Commercial Bovine Testicular Hyaluronidase", 1983 *Thrombosis Research* 30:565–571.

Baumgartner et al., "Hyaluronidase in Combination with Anticancer Drugs—Results of a Pilot Study", 1985, *Wiener Klinische Wochenscrift* 97:148–153.
Horn et al., "Intraversical Chemotherapy of Superficial Bladder Tumors in a Controlled Trial with Cis–Platinum Versus Cis–Platinum Plus Hyaluronidase," 1985, *Journal of Surgical Oncology* 28:304–307.
Barnhart, publ. 1985, *PDR 39$^{th}$ Ed.*, Medical Economics Company, Inc., Ordell, NJ, pp. 2296–2297.
Zanker et al., "Introduction of Response in Previous Chemotherapy Resistant Patients by Hyaluronidase," 1986, *Proceedings of AACR* 27:390, Abstract No. 1550.
Baumgartner, Hyaluronidase in Management of Malignant Diseases, 1987, *Deilage zu Wien Klin Wochenschr 99* by Springer–Verlag/Wien, pp. 3–22.
Baumgartner et al., "Phase I Study in Chemoresistant Logo–regional malignant disease with Hyaluronidase," 1988, *Reg. Cancer Treat.* 1:55–58.
Scheithauer et al., In Vitro Evalutation of the Anticancer Drug Modulatory Effect of Hyaluronidase in Human Gastrointestinal Cell Lines, 1988, *Anticancer Research* 8:391–396.
Baumgartner et al., "Hyaluronidase—an Effective Substance in the Treatment of Malignant Disease," 1988 *5$^{th}$ Medical Department with Oncology*, Vienna City Hospital Lainz, pp. 3–9.
Czejka et al., 1990, *Pharmazie* 45:H.9.
Lace et al., "The Effects of Deglycosylation on the Properties of Native and Biotinylated Bovine Testicular Hyaluronidase," 1990, *Carbohydrate Research* 208:306–311.
Nucci et al., "The Therapeutic Value of Poly(ethylene glycol)–Modified Proteins," 1991 *Adv. Drug Delivery Rev.* 4:133–151.
Clark–Lewis et al., "Chemical Synthesis, Purification, and Characterization of Two Inflammatory Proteins, Neutrophil Activating Peptide 1 (Interleukin–8) and Neutrophil Activating Peptide 2," 1991, *Biochemistry* 30:3128–3135.
Schuller et al., "Pharmacokinetics of Intrahepatic 5–Fluorouracil ± Preinjected Hyaluronidase (Neopermease, N)," 1991, *Amer. Assoc. For Cancer Res.* 32:171, Abstract No. 1034.
Bertrand et al., "Hyaluronan (Hyaluronic Acid) and Hyaluronectin in the Extracellular Matrix of Human Breast Carcinomas: Comparison Between Invasive and Non–Invasive Area," 1991, *Int. J. Cancer* 52:1–6.

(List continued on next page.)

*Primary Examiner*—Rebecca E. Prouty
*Assistant Examiner*—Lisa J. Hobbs
*Attorney, Agent, or Firm*—Carol L. Francis; Bozicevic & Reed LLP

[57]   ABSTRACT

The invention features a purified hyaluronidase BH55 polypeptide isolated from a mammalian species, preferably bovine or human. The invention also features DNA encoding BH55, vectors and transformed host cells containing DNA encoding BH55, methods of making BH55 hyaluronidase polypeptides, and antibodies that specifically bind BH55.

8 Claims, 3 Drawing Sheets

OTHER PUBLICATIONS

Underhill, "CD44: The Hyaluronan Receptor," 1992, *J. Cell Science* 103:293–298.

Gunthert et al., "A New Variant of Glycoprotein CD44 Confers Metastic Potential to Rat Carcinoma Cells," 1991, *Cell* 65:13–24.

De Maeyer et al., "The Growth Rate of Two Transplantable Murine Tumors, 3LL Lung Carcinoma and B16F10 Melanoma, is Influenced by Hyal–1, A Locus Determining Hyaluronidase Levels and Ploymorphism," 1992 *Int. J. Cancer* 51:657–660.

Beckenlehner et al., "Hyaluronidase Enhances the Activity of Adriamycin in Breast Cancer Models In Vitro and In Vivo," 1992, *J. Cancer Res. Clin. Oncol.* 118: 591–596.

Stern et al., "An ELISA–Like Assay for Hyaluronidase and Hyaluronidase Inhibitors," 1992, *Matrix* 12:397–403.

Guntenhoner et al., "A Substrate–Gel Assay for Hyaluronidase Activity," 1992, *Matrix* 12:388–396.

Lin et al., "Molecular Cloning of the Human and Monkey Sperm Surface Protein PH–20," 1993, *Proc. Natl. Acad. Sci. USA* 90:10071–10075.

Knudson et al., "Hyaluronan–Binding Proteins in Development, Tissue Homeostasis, and Disease," 1993 *FASEB J.* 7:1233–1241.

Wielenga et al., "Expression of CD44 Variant Proteins in Human Colorectal Cancer is Related to Tumor Progression," 1993, *Cancer Research* 53:4754–4756.

Joensuu et al., "Glycoprotein CD44 Expression and its Association with Survival in Breast Cancer," 1993, *American Journal of Pathology* 143(3):867–874.

Bartolazzi et al., "Interaction Betweeen CD44 and Hyaluronate is Directly Implicated in the Regulation of Tumor Development," 1994, *J. Exp. Med.,* The Rockefeller University Press 180:53–66.

Zhu et al., "molecular Cloning of Mammalian Hyaluronidase Reveals Identity with Hemopexin, a Serum Heme–binding Protein," 1994, *J. of Biol. Chem.* 269(51):32092–32097.

Yokozaki et al., "Expression of CD44 Abnormal Transcripts in Human Gastric Carcinomas," 1994, *Cancer Letters* 83:229–234.

Kohno et al., "Effects of Hyaluronidase on Doxorubicin Penetration into Squamous Carcinoma Multicellular Tumor Spheroids and its Cell Lethality," 1994, *J. Cancer Res. Clin. Oncol.* 120:293–297.

Arky, Consult., 1994, *PDR 48$^{th}$ Ed.,* medical Economics Data Production Co. Montrale, NJ, pp. 2626–2627.

Frost et al., "A Novel Hyaluronidase Isolated from Bovine Testes," 1995, *FASEB, ASBMB/DBC–ACS* 9(6), Abstract.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:1:

Gly Pro Xaa Pro Ile Tyr His Ile Gln Glu Ala Val Leu
    1                  5                              10

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

Val Leu Xaa Arg Glu Pro Ala Gly Ala Val Ile Xaa Gly Tyr Gly Thr

```
              1               5                    10                    15
        Pro Arg Ala Thr Val Thr Val Thr Leu Xaa Arg
                        20                    25
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

```
        Gly Pro Ser Ala His Ser Val Leu
        1               5
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:4:

```
        Met Lys Lys Gly Thr Arg Val Leu Xaa Asp Ser Asn
        1               5                   10
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

```
        Lys Pro Gly Gly Pro
        1               5
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

```
        Xaa Val Phe Gln Val Phe Val Ala Xaa Gly Glu Leu
        1               5                   10
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

Ser Xaa Phe Xaa Ala Pro Pro Leu Ile Pro Asn
1               5                       10

( 2 ) INFORMATION FOR SEQ ID NO:8:

( i ) SEQUENCE CHARACTERISTICS:
    ( A ) LENGTH: 11 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:8:

Asp Lys Phe Arg Ala Pro Pro Leu Ile Pro Asn
1               5                       10

( 2 ) INFORMATION FOR SEQ ID NO:9:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:9:

GGCCCCNNNC CCATCTACCA CTACCAGGAG GCCGTGCTG    39

( 2 ) INFORMATION FOR SEQ ID NO:10:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:10:

GUUCUGNNNC GUGAACCGGC UGGUGCUGUU AUCNNNGGUU ACGGUACCCC GCGUGCUACC    60

GUUACCGUUA CCCUGNNNCG U    81

( 2 ) INFORMATION FOR SEQ ID NO:11:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:11:

GGUCCGUCCG CUCACUCCGU UCUG    24

( 2 ) INFORMATION FOR SEQ ID NO:12:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:12:

AUGAAAAAAG GUACCCGUGU UAAANNGAC UCCAAC                                                      36

( 2 ) INFORMATION FOR SEQ ID NO:13:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: RNA ( x i ) SEQUENCE DESCRIPTION: SEQ ID NO:13:

AAACCGGGUG GUCCG                                                                             15

( 2 ) INFORMATION FOR SEQ ID NO:14:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( i i ) MOLECULE TYPE: RNA ( x i ) SEQUENCE DESCRIPTION: SEQ ID NO:14:

NNNGUUUUCC AGGUUUUCGU UGCUNNNGGU GAACUG                                                      36

BH55 HYALURONIDASE

This application is a divisional of U.S. patent application Ser. No. 08/419,594, filed Apr. 4, 1995, now U.S. Pat. No. 5,747,025 which application is hereby incorporated by reference.

STATEMENT AS TO FEDERALLY SPONSORED RESEARCH

This invention was made with government support under grant no.s CA44768, CA58207, and GM46765, awarded by the National Institutes of Health. The government may have certain rights in this invention.

FIELD OF THE INVENTION

This invention relates generally to the field of β-1,4-endoglycosidases, particularly hyaluronidases.

BACKGROUND OF THE INVENTION

Hyaluronidases are a group of neutral- and acid-active enzymes found throughout the animal kingdom. There are primarily two classes of hyaluronidases: 1) those which are relatively non-specific and cleave hyaluronic acid, chondroitin, and related polysaccharides; and 2) those which specifically cleave hyaluronic acid. Degradation of hyaluronic acid by hyaluronidase is accomplished by either cleavage at β-N-acetyl-hexosamine-[1→4]-glycosidic bonds or cleavage at β-gluconrate-[1→3]-N-acetylglucosamine bonds.

Hyaluronic acid is an essential component of the extracellular matrix. Hyaluronic acid is found in the connective tissue of mammals and is the main constituent of the vitreous of the eye. In connective tissue, the water of hydration associated with hyaluronic acid creates spaces between tissues, thus creating an environment conducive to cell movement and proliferation. Hyaluronic acid plays a key role in biological phenomena associated with cell motility including rapid development, regeneration, repair, embryogenesis, embryological development, wound healing, angiogenesis, and tumorigenesis (Toole, 1991, *Cell Biol. Extracell.* Matrix, Hay (ed), Plenum Press, N.Y., 1384–1386; Bertrand et al., 1992, *Int. J. Cancer* 52:1–6; Knudson et al., 1993, *FASEB J.* 7:1233–1241). In addition, hyaluronic acid levels correlate with tumor aggressiveness (Ozello et al., 1960, *Cancer Res.* 20:600–604; Takeuchi et al., 1976, *Cancer Res.* 36:2133–2139; Kimata et al., 1983, *Cancer Res.* 43:1347–1354).

CD44, the predominant cell surface receptor for hyaluronic acid (Underhill, 1991 *J. Cell Science* 103:293–298), also plays a key role in cell motility. CD44 is expressed in a variety of isoforms as a result of alternative splicing of the encoding DNA (Gunther et al., 1991, *Cell* 65:13–24). Specific CD44 isoforms confer enhanced cell motility, and are associated with aggressive behavior (e.g., tumor progression and metastasis) in a variety of human malignancies (Bartolazzi et al., 1994, *J. Exp. Med.* 180:53–66; Yokozaki et al., 1994, *Cancer Letters* 83:229–234; Joensuu et al., 1993, *Amer. J. Path.* 143:867–874; Wielenga et al., 1993, *Cancer Res.* 53:4754–4756).

Hyaluronidase inhibits cell motility, and thus tumor metastasis, through its degradative enzymatic activity against hyaluronic acid. In addition, hyaluronidase inhibits expression of motility-enhancing CD44 exons. Thus, hyaluronidase not only removes the environment that facilitates cell movement, but also turns off the intrinsic cell machinery that endows cells with motility.

Hyaluronidase is useful as a therapeutic in the treatment of diseases associated with excess hyaluronic acid and to enhance circulation of physiological fluids and/or therapeutic agents at the site of administration. For example, hyaluronidase has been used to reduce intraocular pressure in the eyes of glaucoma patients through degradation of hyaluronic acid within the vitreous humor (U.S. Pat. No. 4,820,516, issued Apr. 11, 1989). Hyaluronidase has also been used as a "spreading agent" to enhance the activity of chemotherapeutics and/or the accessibility of tumors to chemotherapeutics (Schüller et al., 1991, *Proc. Amer. Assoc. Cancer Res.* 32:173, abstract no. 1034; Czejka et al., 1990, *Pharmazie* 45:H.9). Combination chemotherapy with hyaluronidase is effective in the treatment of a variety of cancers including urinary bladder cancer (Horn et al., 1985, *J. Surg. Oncol.*, 28:304–307), squamous cell carcinoma (Kohno et al., 94, *J. Cancer Res. Oncol.*, 120:293–297), breast cancer (Beckenlehner et al., 1992, *J. Cancer Res. Oncol.* 118:591–596), and gastrointestinal cancer (Scheithauer et al., 1988, *Anticancer Res.* 8:391–396). Hyaluronidase is effective as the sole therapeutic agent in the treatment of brain cancer (gliomas) (PCT published application no. WO88/02261, published Apr. 7, 1988). Administration of hyaluronidase also induces responsiveness of previously chemotherapy-resistant tumors of the pancreas, stomach, colon, ovaries, and breast (Baumgartner et al., 1988, *Reg. Cancer Treat.* 1:55–58; Zanker et al., 1986, *Proc. Amer. Assoc. Cancer Res.* 27:390).

In addition to its indirect anticancer effects, hyaluronidase has direct anticarcinogenic effects. Hyaluronidase prevents growth of tumors transplanted into mice (De Maeyer et al., 1992, *Int. J. Cancer* 51:657–660) and inhibits tumor formation upon exposure to carcinogens (Pawlowski et al., 1979, *Int. J. Cancer* 23:105–109; Haberman et al., 1981, *Proceedings of the 17th Annual Meeting of the American Society of Clinical oncology*, Washington, D.C., 22:105, abstract no. 415).

Given the value of hyaluronidases as a therapeutic, particularly in chemotherapy in conjunction with conventional chemotherapeutics or as a chemotherapeutic in and of itself, there is a need in the field for substantially pure preparations of hyaluronidase. There is also a need for efficient, cost-effective methods of making hyaluronidase to provide commercially significant quantities of the enzyme. The present invention addresses these problems.

SUMMARY OF THE INVENTION

The invention is based upon the discovery that the commercially available bovine testicular extracts contain not one hyaluronidase as previously thought, but rather two hyaluronidases. One of these hyaluronidases, herein termed BH55, has not been described previously.

The present invention features a purified hyaluronidase BH55. The BH55 hyaluronidase is isolated from any mammalian species including bovine, human, canine, equine, feline, preferably bovine or human. In related aspects, the invention features DNA encoding BH55, vectors and transformed host cells containing DNA encoding BH55, a method of producing BH55 polypeptides, and an injectable composition containing a substantially pure BH55 hyaluronidase polypeptide.

The invention also features antibodies that specifically bind BH55 and assays which use these antibodies to detect BH55.

A primary object of the invention is to provide a purified hyaluronidase, BH55, which may be used in a variety of clinical therapies including cancer therapy and treatment of glaucoma.

Another object of the invention is to provide recombinantly expressed BH55 for use in various clinical therapies.

An advantage of the present invention is that purified BH55 is more appropriate for therapeutic uses than the presently available commercial formulations of hyaluronidase which contain two hyaluronidases, rather than one. Furthermore, as determined by SDS-PAGE analysis, the commercial formulation is a very crude mixture that contains various proteins, including several unidentified proteins and proteins having various biological activities including anticoagulant activities (Doctor et al., *Thrombosis Res.* 30:565–571). Purified BH55, either native or recombinant, provides a "clean" source of hyaluronidase, is less likely to induce some of the side effects associated with the presently available commercial formulation, and allows better control of the level of activity associated with specific dosages.

Another advantage of the invention is that BH55 hyaluronidase can be produced by recombinant means, thus providing a more cost-efficient method of producing the enzyme than purification of the enzyme from, for example, bovine testicular extracts.

These and other objects, advantages and features of the present invention will become apparent to those persons skilled in the art upon reading the details of the invention as more fully set forth below.

DESCRIPTION OF THE PREFERRED EMBODIMENTS

Figure 1:
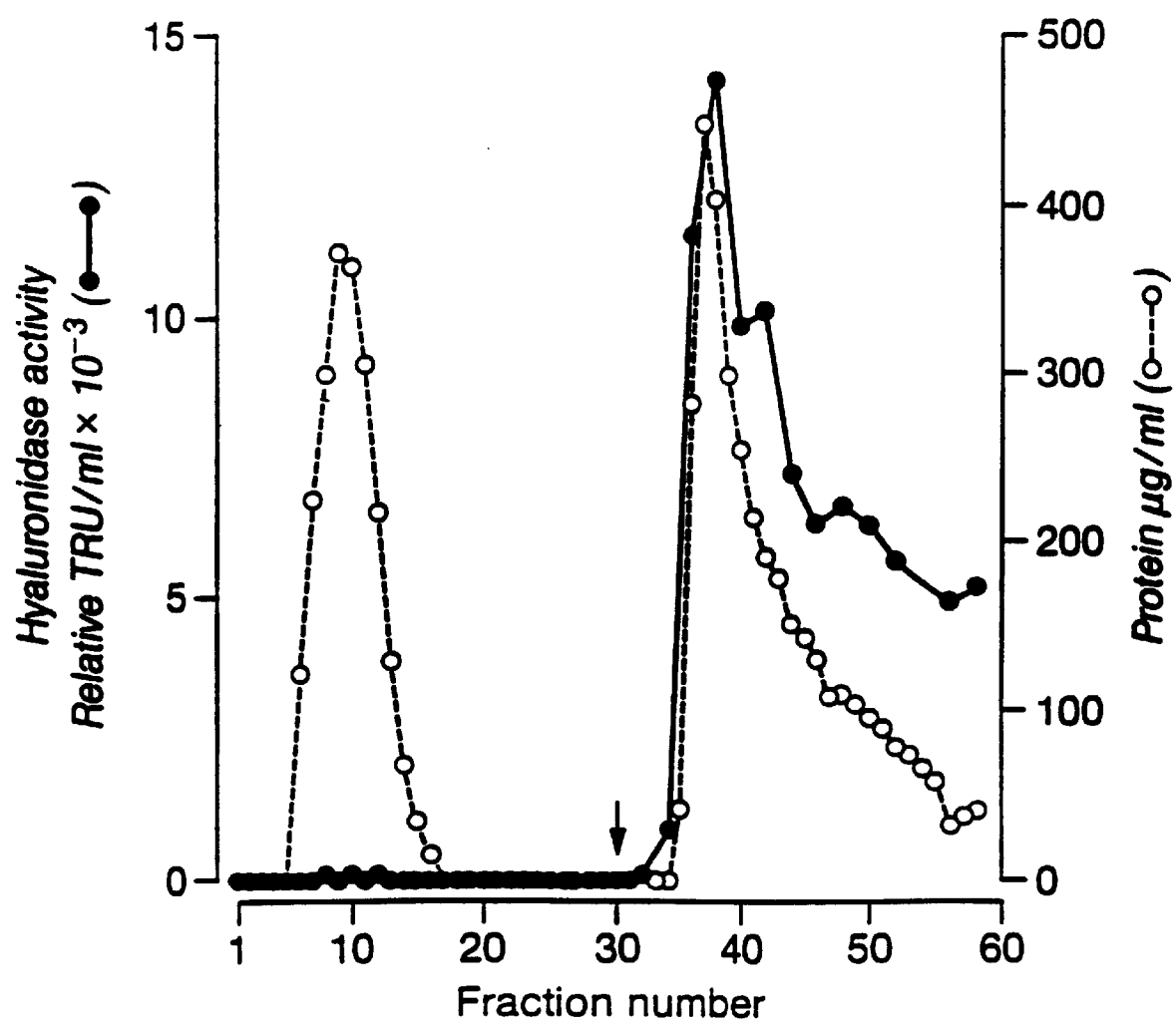
FIG. 1 is a graph showing the elution profile of hyaluronidase on Concanavalin-A column chromatography. The arrow indicates the addition of 0.6 M alpha-methyl-pyranoside. Closed circles indicate hyaluronidase activity associated with each fraction tested. Open circles indicate the protein concentration of each fraction.

Before the present purified BH55 hyaluronidase and DNA encoding same are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a transformed cell containing DNA encoding a BH55 hyaluronidase" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

Definitions

By "BH55" is meant a hyaluronidase having the following characteristics: 1) β-1,4-endoglycosidase activity in the cleavage of hyaluronic acid; 2) a molecular weight ranging from about 14 kDa, to 55 kDa, and having a molecular weight of about 55 kDa as determined by 12.5% SDS-PAGE non-reducing gel electrophoresis; 3) immunological cross-reactivity with an anti-porcine liver hyaluronidase antibody; 4) a specific enzymatic activity of about $70 \times 10^3$ turbidity reducing units (TRU)/mg protein following purification; 5) is stabilized in 1 mg/ml poly vinyl alcohol, sodium chloride; 6) is inhibited in hyaluronidase activity in the presence of heparin or melittin; 7) is destabilized at a pH below 4.0, and loses over 70% of its enzymatic activity after a one hour incubation at pH 3.5 at 37° C.; and 8) contains the amino acid sequences:

a) Gly-Pro-Xaa-Pro-Ile-Tyr-His-Ile-Gln-Glu-Ala-Val-Leu (SEQ ID NO: 1) (within the N-terminus of the protein);

b) Val-Leu-Xaa-Arg-Glu-Pro-Ala-Gly-Ala-Val-Ile-Xaa-Gly-Tyr-Gly-Thr-Pro-Arg-Ala-Thr-Val-Thr-Val-Thr-Leu-Xaa-Arg; (SEQ ID NO: 2);

c) Gly-Pro-Ser-Ala-His-Ser-Val-Leu; (SEQ ID NO: 3);

d) Met-Lys-Lys-Gly-Thr-Arg-Val-Lys-Xaa-Asp-Ser-Asn; (SEQ ID NO: 4);

e) Lys-Pro-Gly-Gly-Pro; (SEQ ID NO: 5); and f) Xaa-Val-Phe-Gln-Val-Phe-Val-Ala-Xaa-Gly-Glu-Leu. (SEQ ID NO: 6). BH55 hyaluronidase is a separate enzyme distinct from PH20 hyaluronidase and can originate from any mammalian species.

By "a BH55 polypeptide" is meant a polypeptide having an amino acid sequence substantially identical to the amino acid sequence of native BH55, or a biologically active polypeptide fragment thereof.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

By a "substantially pure polypeptide" is meant a BH55 polypeptide which has been separated from components which naturally accompany it (e.g., a substantially pure BH55 hyaluronidase polypeptide purified from bovine testicular extracts is substantially free of bovine testicular hyaluronidase PH20). Typically,-the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, BH55 polypeptide. A substantially pure BH55 polypeptide may be obtained, for example, by extraction from a natural source (e.g., a bovine testicular extract); by expression of a recombinant nucleic acid encoding BH55 polypeptide; or by chemically synthesizing the protein. Purity can be measured by any appropriate method, e.g., chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eucaryotic organisms but synthesized in E. coli or other prokaryotes.

By "purified antibody" is meant one which is sufficiently free of other proteins, carbohydrates, and lipids with which it is naturally associated. Such an antibody "preferentially binds" to BH55 hyaluronidase (or a fragment thereof) of the invention, i.e., does not substantially recognize and bind to other antigenically-unrelated molecules.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a DNA of interest (e.g., DNA encoding a BH55 polypeptide) and a regulatory sequence(s) are connected in such a way as to permit gene expression of the DNA of interest when the appropriate molecules (e.g., transcriptional activator proteins) are bound to the regulatory sequence(s), thus facilitating production of, e.g., a BH55 polypeptide, a recombinant protein, or an RNA molecule.

By "transformation" is meant a permanent genetic change induced in a cell following incorporation of new DNA (i.e., DNA exogenous to the cell). Where the cell is a mammalian cell, the permanent genetic change is generally achieved by introduction of the DNA into the genome of the cell.

By "transformed cell" is meant a cell into which (or into an ancestor of which) has been introduced, by means of recombinant DNA techniques, a DNA molecule encoding a BH55 hyaluronidase peptide of the invention.

By "vector" is meant any compound, biological or chemical, which facilitates transformation of a host cell with DNA encoding a BH55 hyaluronidase polypeptide of the invention.

By "therapeutically effective amount of a substantially pure BH55 hyaluronidase polypeptide" is meant an amount of a substantially pure BH55 hyaluronidase polypeptide effective to facilitate degradation of hyaluronic acid in a subject in the treatment of a condition associated with excess hyaluronic acid, undesirable cell motility (e.g., tumor cell metastasis), and/or to enhance circulation of physiological fluids at the site of administration.

The invention will now be described in further detail.

Purification of BH55

BH55 hyaluronidase can be purified from a mammalian testicular extract using a variety of methods well known in the protein purification art (see, for example, Deutscher, ed., 1990, "Guide to Protein Purification," Academic Press, Inc., San Diego, Calif.). For example, BH55 can be purified from a bovine testicular extract by chromatography (e.g., cation exchange chromatography, FPLC, immunoaffinity chromatography). Preferably, purified BH55 hyaluronidase does not contain a significant amount of PH20 hyaluronidase. Preferably, prior to chromatographic purification a sample containing BH55 is reduced by exposure to a reducing agent (e.g., dithiothreitol) and treated with serine proteinase inactivators (e.g., PMSF).

Bovine testicular BH55 hyaluronidase can be purified from a commercial preparation through sequential affinity chromatography on Concanavalin-A Sepharose, cation exchange on MONO-S (FPLC), and gel filtration on Superose 12 (FPLC). Alternatively, bovine testicular BH55 hyaluronidase can be purified from an acetone powder dehydrated extract of bovine testis using acid treatment, ammonium sulfate precipitation, chloroform treatment, and ion exchange. DEAE-cellulose chromatography (Sour et al., 1963, Biothim. Biophys. Acta. 69:538–543; Sour et al., 1963, Arch. Roum. Pathol. Expt. Microbiol. 22:783–790). BH55 hyaluronidase purified from this source is about 42 kDa and has enzymatic activity.

In one example, BH55 was purified from a reduced sample of a bovine testicular extract (Sigma, St. Louis, Mo.) by a combination of chromatography and gel filtration. The sample containing BH55 was applied to a Concanavalin-A column (Pharmacia, Piscataway, N.J.). Fractions containing hyaluronidase activity were pooled. The pooled samples were then applied to a Mono-S cation exchange column. The active fractions containing hyaluronidase activity after Mono-S chromatography were again pooled and applied to two subsequent Superose-12 FPLC columns. The fractions corresponding to each peak of activity were pooled and the protein in peak fractions further characterized.

Assays for hyaluronidase activity

Hyaluronidase activity can be monitored using a modified version of an ELISA-like assay for hyaluronidase activity (Stern et al., 1992, Matrix 12:391–403) wherein a sample containing hyaluronidase is applied to the well of a microtiter dish having hyaluronic acid bound to its surface.

Hyaluronidase activity is detected by the amount of undigested hyaluronic acid remaining in the well after incubation with the sample. This method is 1,000 to 10,000 times more sensitive in the detection of hyaluronidase activity than the conventional Reissig assay (Reissig et al., 1955, *J. Biol. Chem.* 217:956–966).

Hyaluronidase activity can also be detected by substrate gel zymography (Guentenhoner et al., 1992, *Matrix* 388–396). In this assay a sample is applied to a SDS-PAGE gel containing hyaluronic acid and the proteins in the sample separated by electrophoresis. The gel is then incubated in an enzyme assay buffer and subsequently stained to detect the hyaluronic acid in the gel. Hyaluronidase activity is visualized as a cleared zone in the substrate gel.

The specific activity of hyaluronidase is expressed in turbidity reducing units (TRU). One TRU is defined as the amount of hyaluronidase activity required to reduce the turbidity of an acidified solution of hyaluronic acid and is equivalent to the U.S.P./National Formulary (NF XIII) units (NFU). The ELISA-like enzyme assay used for purification is related to the TRU, the NFU, and U.S.P. unit through a standard curve of a sample of hyaluronidase (e.g., Wydase) standardized through the U.S.P. Therefore, the enzyme activities determined by the ELISA-like enzyme assay are actually relative TRU, since enzyme activity is not actually measured using the turbidometric assay (Dorfman et al., 1948, *J. Biol. Chem.* 172:367).

Methods of Making BH55 Hyaluronidase

In addition to the purification procedure outlined above, BH55 hyaluronidase polypeptides can be made by standard synthetic techniques, or by using recombinant DNA technology and expressed in bacterial, yeast, or mammalian cells using standard techniques. As used herein, the term "BH55 hyaluronidase" includes both the natural and recombinant forms of the protein.

Chemical Synthesis

BH55 hyaluronidase polypeptides can be synthesized based on the amino acid sequences described herein and variations thereof by standard solid-phase methods using the tert-butyloxy-carbonyl and benzyl protection strategy described in Clark-Lewis et al., *P.N.A.S., USA,* 90:3574–3577 (1993) and Clark-Lewis et al., *Biochemistry,* 30:3128–3135 (1991). After deprotection with hydrogen fluoride, the proteins are folded by air oxidation and purified by reverse-phase HPLC. Purity is determined by reverse-phase HPLC and isoelectric focusing. Amino acid incorporation is monitored during synthesis, and the final composition is determined by amino acid analysis. The correct covalent structure of the protein can be confirmed using ion-spray mass spectrometry (SCIEX APIII).

Recombinant DNA Techniques for Synthesis of BH55 Hyaluronidase Polypeptides

The gene encoding BH55 hyaluronidase can be isolated according to any one of a variety of methods well known to those of ordinary skill in the art. For example, DNA encoding BH55 hyaluronidase can be isolated from either a cDNA library (e.g., prepared from bovine testicular RNA) or from a genomic DNA library (e.g., a bovine genomic library) by either hybridization or expression cloning methods. Alternatively, the DNA may be isolated using standard polymerase chain reaction (PCR) amplification of synthetic oligonucleotide primers, e.g., as described in Mullis et al., U.S. Pat. No. 4,800,159.

Where hybridization is used to identify DNA encoding BH55 hyaluronidase, the sequence of the oligonucleotide probes may be based upon an amino acid sequence of a purified BH55 hyaluronidase (e.g., an amino acid sequence determined by sequencing an N-terminal fragment or a fragment generated by cyanogen bromide degradation). Degenerate oligonucleotide probe design can take into account the frequency of codon use in the mammalian species DNA to be screened. For example, where the probe is designed to identify DNA encoding a bovine protein, the frequency of codon usage in bovine DNA is considered in oligonucleotide design. Likewise, if the DNA to be screened is human DNA, the frequency of codon usage in DNA encoding human proteins is considered in probe design. Such "degenerate oligonucleotide probes" can be used in combination in order to increase the sensitivity of the hybridization screen. Methods for designing and using degenerate oligonucleotide probes to identify a protein for which a partial amino acid sequence is known are routine and well known in the art (see, for example, Sambrook et al., 1989, *Molecular Cloning: A Laboratory Manual,* 2nd Ed., Cold Spring Harbor Laboratory Press, Cold Spring Harbor, N.Y.).

Alternatively, the DNA encoding hyaluronidase may be isolated by expression cloning methods well known in the art (see, for example, Sambrook et al., supra). For example, bacteria may be transformed with a cDNA expression library, i.e., a collection of clones containing various cDNA fragments operably linked to a procaryotic promoter. Bacterial expression of a BH55 hyaluronidase or a biologically active fragment thereof can be detected by assaying the culture supernatant and/or cell lysates using the ELISA-like hyaluronic assay described above. Alternatively, production of BH55 hyaluronidase or an antigenic portion thereof may be detected by the binding of an anti-BH55 hyaluronidase antibody to a component of the bacterial cell supernatant and/or lysate.

Where DNA encoding a BH55 hyaluronidase is isolated using PCR, degenerate oligonucleotide primers can be designed and synthesized as described above for hybridization cloning. The oligonucleotide primers are combined with a sample containing the target DNA and the DNA amplified by several cycles of PCR. Following amplification, the selected amplified DNA is electrophoresed on a low-melting point agarose gel and bands corresponding to the DNA of interest are excised from the gel and ligated into the desired expression vector according to methods well known in the art (see, for example, Sambrook et al., supra; U.S. Pat. No. 4,800,159).

The nucleotide sequence of the BH55 hyaluronidase polypeptide-encoding DNA can be determined using methods well known in the art (see, for example, Sambrook et al., supra). Following sequence confirmation, the resulting plasmid clones are used to identify the full-length gene, identify homologs of a BH55 hyaluronidase (e.g., a BH55 hyaluronidase of another mammalian species), and/or to transform the desired host for expression of the BH55 hyaluronidase-encoding DNA. For example, upon identification of DNA encoding bovine testicular BH55 hyaluronidase, the DNA can be used as a hybridization probe to identify the human BH55 homolog.

Vectors and Constructs for Expression of BH55 Hyaluronidase Polypeptides

Any nucleic acid vector having a promoter which can be operably linked to a DNA encoding a BH55 hyaluronidase polypeptide of the invention can be used to transform a mammalian, yeast, or bacterial host cell. For example, a plasmid having a bacterial origin of replication can be cleaved to provide linear DNA having ligatable termini. These termini are bound to exogenous DNA having complementary, like ligatable termini to provide a biologically functional, BH55 hyaluronidase polypeptide recombinant DNA molecule.

Various vectors (e.g., bacterial vectors, yeast vectors, eucaryotic vectors, or vectors capable of replication in eucaryotic and procaryotic hosts) can be used in accordance with the present invention. Preferably the vector is capable of replication in both eucaryotic and procaryotic hosts. Numerous vectors that can replicate in eucaryotic and procaryotic hosts are known in the art and are commercially available. In general, such vectors used in accordance with the invention are composed of a bacterial origin of replication and a eucaryotic promoter operably linked to a DNA of interest.

A variety of techniques are available for DNA recombination in which adjoining ends of separate DNA fragments are tailored to facilitate ligation. The vector is constructed using known techniques to obtain a transformed cell capable of expression of the BH55 hyaluronidase polypeptide. Techniques for obtaining expression of exogenous DNA or RNA sequences in a host cell are well known in the art (see, for example, Kormal et al., 1987, Proc. Natl. Acad. Sci. USA, 84:2150–2154; Sambrook et al., supra; each of which are hereby incorporated by reference with respect to methods and compositions for eucaryotic expression of a DNA of interest).

BH55 Hyaluronidase Polypeptide Expression

BH55 hyaluronidase polypeptides according to the invention can be produced by transformation of a suitable host cell (e.g., bacterial, yeast, or mammalian cell) with a BH55 hyaluronidase polypeptide-encoding DNA-fragment in a suitable expression vehicle, and culturing the transformed cells under conditions that promote expression of the polypeptide encoded by the DNA fragment. The method of transformation and the choice of expression vehicle will depend on the host system selected. Those skilled in the field of molecular biology will understand that any of a wide variety of procaryotic and eucaryotic expression systems may be used to produce BH55 hyaluronidase polypeptides of the invention. The precise host cell used is not critical to the invention. Preferably, the host cell is a *Saccharomyces cerevisiae* yeast strain or a CHO-cell line, more preferably a CHO cell line or a CHO-cell derived cell line.

A number of vectors suitable for stable transfection of mammalian, yeast and bacterial cells are available to the public from a wide variety of sources, e.g., the American Type Culture Collection, Rockville, Md. Suitable host cells, as well as methods for constructing stably-transformed host cell lines, are also publicly available, e.g., Pouwels et al., 1985, *Cloning Vectors*: A Laboratory Manual, Ausubel et al., 1989, *Current Protocols in Molecular Biology*, John Wiley & Sons, New York; and Sambrook et al., supra.

For example, cDNA encoding a BH55 hyaluronidase polypeptide is cloned into an expression vector which includes the dihydrofolate reductase (DHFR) gene. Integration of the plasmid and, therefore, the BH55 hyaluronidase-encoding DNA into the mammalian host cell chromosome is selected for by inclusion of 0.01–300 $\mu$M methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include PCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

Expression of recombinant BH55 hyaluronidase polypeptide (e.g., produced by any of the expression systems described herein) can be assayed by immunological procedures, such as Western blot or immunoprecipitation analysis of recombinant cell extracts, or by the hyaluronidase activity assay described herein (Stern et al., 1992, *Matrix* 12:391–403)).

Identification of Biologically Active BH55 Hyaluronidase Polypeptides

BH55 polypeptide-encoding DNAs of the invention may encode all or a portion of a BH55 hyaluronidase. Preferably, the BH55 polypeptide will be biologically active, i.e., exhibit hyaluronidase activity in the cleavage of hyaluronic acid. Biologically active polypeptides of BH55 hyaluronidase can be identified by expression of fragments of the wild-type DNA encoding native BH55 hyaluronidase. Biologically activity of the BH55 polypeptides can be assayed using the ELISA-like hyaluronic acid assay (Stern et al., 1992, *Matrix* 12:391–403) or by substrate gel zymography (Guentenhoener et al., 1992, Matrix 1:388–396) as described above. BH55 hyaluronidase polypeptides will exhibit at least 25%, preferably 50%, more preferably 75%, even more preferably 95% of the activity of native BH55 hyaluronidase.

Identification of DNA Encoding Hyaluronidases Homologous to a BH55 Hyaluronidase DNA encoding hyaluronidases that are homologous to BH55 hyaluronidase (e.g., contain conservative amino acid substitutions relative to a native BH55 hyaluronidase) can be accomplished by screening various cDNA or genomic DNA libraries by hybridization using oligonucleotides based upon the DNA sequence and/or amino acid sequence of a BH55 hyaluronidase. The oligonucleotides may be designed upon an actual DNA sequence of BH55 hyaluronidase. Alternatively the oligonucleotides used in the hybridization screen may be degenerate, e.g., are based upon a selected amino acid sequence of BH55 hyaluronidase or are designed so as to allow hybridization to DNA encoding a BH55 hyaluronidase-like amino acid sequence having conservative amino acid substitutions. Methods for hybridization screening and isolation of homologous DNAs so identified are routine and well known in the art (see for example, Sambrook et al., supra).

Production of Anti-BH55 Hyaluronidase Antibodies

Polyclonal antibodies and/or monoclonal antibodies that specifically bind BH55 hyaluronidase can be generated according to methods well known and routine in the art (see, for example, Harlow and Lane, 1988, *Antibodies: A Laboratory Manual*, Cold Spring Harbor Laboratory Press, Cold Spring Harbor, N.Y.; Schrier et al., 1980, *Hybridoma Techniques*, Cold Spring Harbor Laboratory Press, Cold Spring Harbor, N.Y.).

Modification of BH55 for therapeutic administration Where BH55 hyaluronidase is to be used in therapy, e.g., chemotherapy, it may be desirable to increase the serum half-life of the protein. Various methods for increasing the half-life of a protein are well known in the art and include, for example, conjugation of the protein to polyethylene glycol moieties, i.e., PEGylation (see, for example, U.S. Pat. No. 4,179,337; U.S. Pat No. 5,166,322; U.S. Pat. No. 5,206,344; Nucci et al., 1991, *Adv. Drug Delivery Rev.* 4:133–151; Zalipsky et al., 1991, "Polymeric Drugs and Drug Delivery Systems," ACS) conjugation of the protein to dextran (Maksimenko, 1986, *Bull. Exp. Biol. Med.* (Russian) 52:567–569), and deglycosylation of the protein by treatment with endoglycosidase F (Lace et al., 1990, *Carbohydrate Res.* 208:306–311).

In general, these methods are designed to increase the molecular weight of the protein, decrease the sensitivity of the protein to proteinases, and/or decrease the rate of clearance of the protein from the subject to be treated. The increased half-life of modified BH55 hyaluronidase polypeptides decreases the amount of protein needed for an effective dosage, reduces the number and frequency of administrations required, and decreases the patient's exposure to the protein, thus decreasing the potential for allergic reactions, toxic effects, or other side effect. These characteristics of modified BH55 hyaluronidase polypeptides having an increased half-life also allow for long-term use of the protein with less potential for undesirable side effects related to protein immunogenicity and/or toxicity. Preferably these methods can be used so that the half-life of the protein is increased without substantially compromising the protein's biological activity. The enzymatic activity of modified BH55 hyaluronidase can be assayed using the ELISA-like hyaluronic acid assay and the substrate gel zymography assay described above.

For example, dextran-modified bovine hyaluronidase has been produced and used successfully in clinics as an inhalation therapeutic with prolonged effectiveness for the treatment of pulmonary fibrosis (Maksimenko, supra). This dextran-modified enzyme has prolonged effectiveness relative to the unmodified parent enzyme. Nucci et al. (supra) describe several therapeutic proteins which have been successfully modified by PEGylation.

The biological half-life (e.g., half-life of the protein in circulation) of a BH55 hyaluronidase polypeptide can be measured by standard methods well known in the art. For example, radioactive modified BH55 hyaluronidase is injected into a mouse, rat, or rabbit. At various times, blood is withdrawn and the amount of BH55 hyaluronidase remaining in circulation is determined by scintillation counting. Alternatively, BH55 hyaluronidase is injected into a mouse, rat, or rabbit. At various times, blood is withdrawn and enzymatic activity in the cleavage of hyaluronic acid is measured. In some cases, the amount of BH55 hyaluronidase polypeptide remaining in circulation can be measured in an immunoassay, e.g., by ELISA. The amount of BH55 hyaluronidase polypeptide can also be determined by detecting a label attached to the protein, e.g., a bioton label. Further, SDS-PAGE and/or modified Western blot techniques can be used to confirm that the labeled enzyme is intact and that the label is not associated with a degradation product.

Use of BH55 Hyaluronidase

The substantially pure BH55 hyaluronidase polypeptides (e.g., BH55 hyaluronidase peptides which are not in association with PH20 hyaluronidase) and modified BH55 hyaluronidase polypeptides (having an increased biological half-life) of the invention can be used in a variety of applications including human and veterinary therapies, either alone or in combination with other therapeutic agents, in the treatment of diseases associated with excess hyaluronic acid and/or to enhance circulation of physiological fluids at the site of administration. For example, BH55 hyaluronidase can be administered to a patient to facilitate clysis, particularly hypodermoclysis. BH55 hyaluronidase can also be administered to patients suffering from stroke or a myocardial infarction. Preferably, BH55 hyaluronidase is administered in the absence, or at very low levels, of heparin, a powerful inhibitor of hyaluronidase.

BH55 hyaluronidase can also be used in the treatment of edema associated with brain tumors, particularly that associated with glioblastoma multiforme. The edema associated with brain tumors results from the accumulation of hyaluronic acid in the non-cancerous portions of the brain adjacent the tumor. Administration of hyaluronidase to the sites of hyaluronic acid accumulation (e.g., by intravenous injection or via a shunt) can relieve the edema associated with such malignancies by degrading the excess hyaluronic acid at these sites. Thus, hyaluronidase is successful in the treatment of brain tumors not only in the reduction of the tumor mass and inhibition of tumor growth and/or metastasis, but it also is useful in relieving edema associated with the malignancy.

Of particular interest is the use of BH55 hyaluronidase polypeptides, especially BH55 hyaluronidase polypeptides modified so as to increase the enzyme's serum half-life relative to unmodified BH55, in the treatment of cancer. BH55 hyaluronidase can be used as a chemotherapeutic agent (alone or in combination with other chemotherapeutics) in the treatment of any of a variety of cancers, particularly invasive tumors. For example, BH55 hyaluronidase polypeptides may be used in the treatment of cancer of the urinary bladder, breast, brain (gliomas), prostate, pancreas, stomach, colon, and ovaries, as well as squamous cell carcinoma. BH55 hyaluronidase can also be used to increase the sensitivity of tumors that are resistant to conventional chemotherapy.

The route of administration and amount of BH55 hyaluronidase administered will vary widely according to the disease to be treated, and various patient variables including size, weight, age, disease severity, and responsiveness to therapy. Methods for determining the appropriate route of administration and dosage are generally determined on a case-by-case basis by the attending physician. Such determinations are routine to one of ordinary skill in the art (see, for example; *Harrison's Principles of Internal Medicine,* 11th Ed., 1987). For example, where BH55 hyaluronidase is used to facilitate hypodermoclysis, a solution containing BH55 hyaluronidase is administered by subcutaneous injection to facilitate absorption of the solution (e.g., nutrient, body fluid replacement, or blood pressure increasing solution). Preferably, BH55 hyaluronidase is administered by injection, e.g., parenteral injection including subcutaneous, intramuscular, intraorbital, intracapsular, and intravenous injection.

The specific dosage appropriate for administration is readily determined by one of ordinary skill in the art according to the factors discussed above (see, for example, *Harrison's Principles of Internal Medicine,* 11th Ed., 1987). In addition, the estimates for appropriate dosages in humans may be extrapolated from determinations of the level of enzymatic activity of a BH55 hyaluronidase in vitro and/or dosages effective in animal studies. For example, 70–300 TRU hyaluronidase is effective in reducing the tumor load in a scid mouse. Given this information, the corresponding dosages in the average 70 kg human would range from about 250,000–1,200,000 TRU hyaluronidase. The amount of BH55 hyaluronidase polypeptide administered to a human patient is generally in the range of 1 TRU to 5,000,000 TRU of enzymatic activity, preferably between about 1,000 TRU to 2,500,000 TRU, more preferably between about 100,000 TRU to 1,500,000 TRU, normally between about 250,000 TRU and 1,200,000 TRU, with about 725,000 TRU representing average prescribed doses.

In general, a BH55 hyaluronidase of the invention is formulated in a 0.15 M saline solution containing BH55 at a concentration of about 150,000 TRU/cc. The formulation is then injected intravenously at 15,000 TRU/kg body weight of the patient. Alternatively, the enzyme formulation may also be injected subcutaneously to allow the hyaluronidase to perfuse around the tumor site.

Numerous other uses for BH55 hyaluronidase, anti-BH55 hyaluronidase antibodies, and DNA encoding BH55 hyaluronidase polypeptides are readily apparent to one of ordinary skill in the art. For example, BH55 hyaluronidase polypeptides can be produced and labeled for use in competition binding assays to detect and/or quantitate hyaluronidases in a sample. Antibodies specific for BH55 hyaluronidase polypeptides can be used in assays to detect BH55 hyaluronidase in samples such as, for example, serum samples of patients receiving BH55 hyaluronidase therapy. Such BH55 hyaluronidase assays may be performed to achieve either qualitative or quantitative results. DNA encoding BH55 hyaluronidase polypeptides can be used in hybridization screening methods to detect other hyaluronidases having homology to BH55 hyaluronidase.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

EXAMPLE 1
Purification of BH55 from bovine testicular extracts

A BH55 hyaluronidase was purified from a commercial preparation of bovine testicular hyaluronidase (Sigma, Type VI-S) by a combination of chromatography and gel filtration. Throughout purification, hyaluronidase activity and protein concentration of the fractions were followed.

Assay for hyaluronidase activity

Hyaluronidase activity was monitored using a modified version of an ELISA-like assay for hyaluronidase activity (Stern et al., 1992, *Matrix* 12:391∝403). Briefly, 10 µg/well (0.1 mg/ml) of human umbilical cord hyaluronic acid (ICN Biochemicals, Costa Mesa, Calif.) was coated into 96-well Covalink-NH plates (Nunc, Placerville, Ohio) and covalently bound through a 1-ethyl-3-(3-dimethylaminopropyl) -carbodiimide (Sigma, St. Louis Mo.) reaction, incubated at 4° C. overnight. Unbound hyaluronic acid was washed from the plates and samples of hyaluronidase were incubated, 100 µl/well, in 0.1 M Na Formate, pH 4.5 with 0.02% crystalline BSA (Promega, Madison, Wis.) and 1 mM saccharolactone (to inhibit exoglycosidase activity) in triplicate for 60 min at 37° C. Remaining undigested hyaluronic acid on the plate was quantified through the use of a bovine nasal cartilage-derived biotinylated hyaluronic acid binding protein (Levvy et al., 1966, *Method Enzymol.* 8:571–584) that was detected through an avidin-biotin-beroxidase reaction with an o-phenylenediamine substrate (Calbiochem), read at 492 nM on a Titerteck Plate Reader. Optical densities were correlated to relative TRU through four parameter curve fit analysis with a testicular hyaluronidase (WYDASE®) of known TRU incubated under identical conditions. WYDASE® (Wyeth-Ayerst, approx. 1050 TRU/mg) was routinely employed for generating the standard curves of enzyme assays.

Determination of protein concentration

The amount of total protein during purification was quantified in two ways, through absorbance at 280 nm and by the Biorad (Burlingame, Calif.) protein microassay kit (Tengblad, 1979, *Biochim. Biophys.* Acta 578:281–289) in 96 well plates, using crystallized bovine serum albumin as a standard and read at 595 nM.

Purification of BH55 hyaluronidase was accomplished as follows:

1) Reduction of oxidized cysteines and inactivation of serine proteases

Approximately 180,000 TRU of lyophilized testicular hyaluronidase (Sigma Type VI-S) was brought to volume in 3 ml of 50 mM Hepes pH 7.5, 1 mg/ml PVA (Sigma P-8136), 1 M NaCl, 0.05% v/v Tween-20 (Fisher Scientific, Pittsburgh, Pa.), 1 mM PMSF (Eastman Kodak, Rochester, N.Y.), 10 mM dithiothreitol (Fisher), and kept on ice for 1 hour. After one hour, 3 ml of reduced and serine protease inactivated bovine testicular extract was passed over an Econo Pac-1ODG desalting column (Biorad) equilibrated with 50 mM Hepes, pH 7.5, 1 M NaCl, 1 mM $CaCL_2$, 1 mM $MnCl_2$ to remove excess PMSF and DTT and prepare for chromatography.

2) Concanavalin-A chromatography

Approximately 12 mg of protein from the desalting column was loaded on a Concanavalin-A (Pharmacia, Piscataway, N.J.) column (4×1 $cm^2$), Equilibrated with 50 mM Hepes pH 7.5, 1 mg/ml PVA, 1 mM $CaCl_2$, 1 mM $MnCl_2$, 1 M NaCl, at a flow rate of 10 ml/hour, collecting 1 ml fractions. The column was washed with 20 ml of the equilibration buffer, followed by 40 ml of buffer containing 0.6 M alpha-methyl pyranoside. Fractions containing activity were pooled, and concentrated using an Amicon 10 kDa cutoff membrane.

The elution profile of the sample from the Concanavalin-A column is shown in FIG. 1. The line with the closed circles indicates the hyaluronidase activity with each fraction assayed. The line with open circles indicates the protein concentration in each fraction assayed. The arrow indicates the addition of alpha-methyl pyranoside.

3) Mono-S cation exchange chromatography

The concentrated material containing hyaluronidase activity from the Concanavalin-A column (fractions 35–50) was passed through a desalting column equilibrated with 50 mM Hepes buffer pH 7.5, 1 mg/ml PVA, 0.05% Tween. The protein fraction of the eluent was loaded on a Pharmacia FPLC Mono-S cation exchanger at a flow rate of 0.5 ml/min, collecting 0.5 ml fractions. The enzyme was then eluted with a gradient of 0.5 M NaCl in 50 mM Hepes, pH 8.2 plus detergent.

Figure 2:
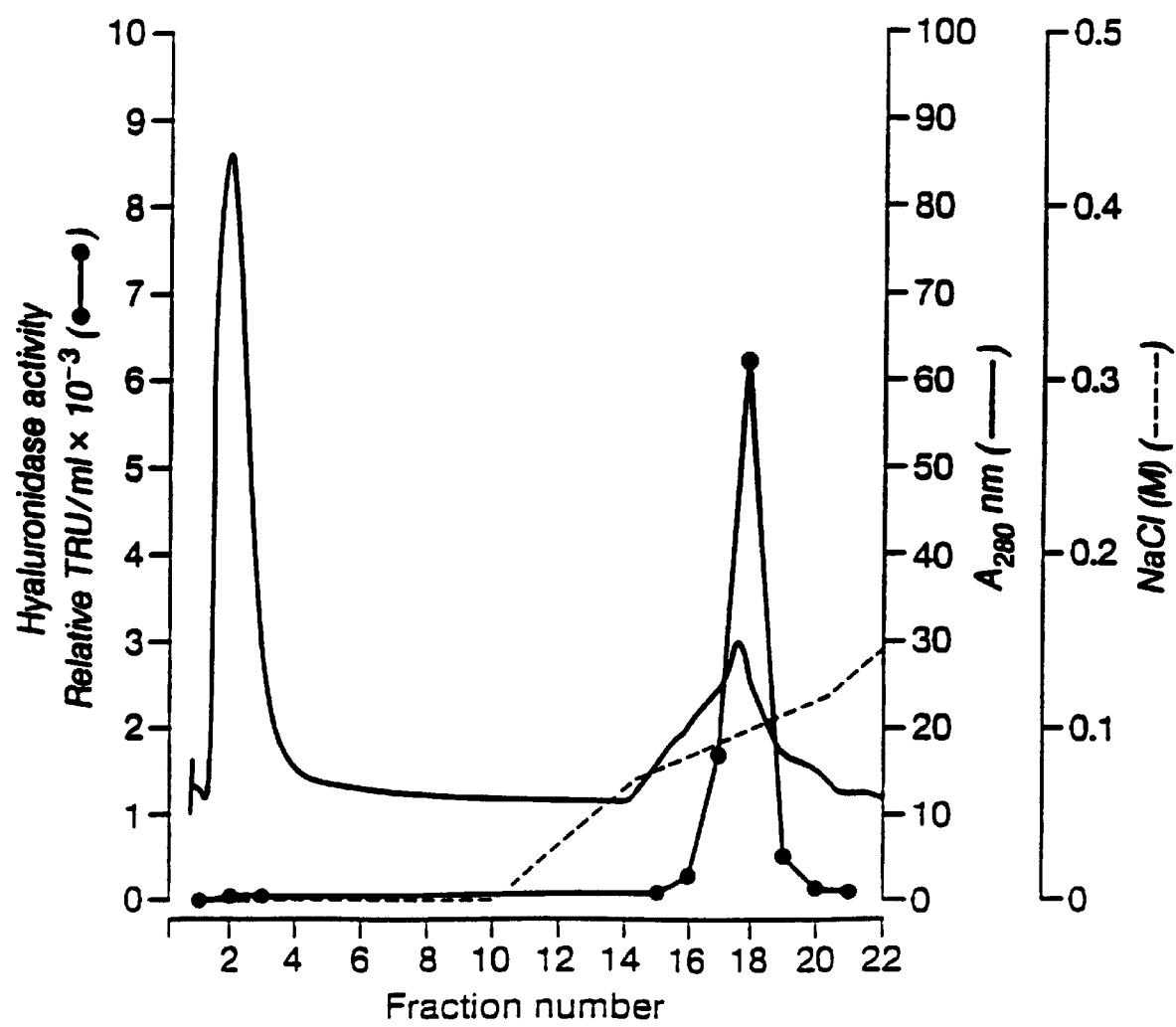
FIG. 2 is a graph showing the elution profile of Concanavalin-A active fractions on Mono-S cation exchange FPLC chromatography. Closed circles indicate hyaluronidase activity associated with each fraction tested. The plain line (no circles) indicates protein concentration. The dashed line indicates the concentration of NaCl in the salt gradient.

FIG. 2 shows the Mono-S cation exchanger elution profile of the sample. The line with the closed circles indicates the hyaluronidase activity of each fraction assayed, while the plain line (no circles) Indicates the protein concentration. The dashed line represents the concentration of sodium chloride in the salt gradient (NaCl 0–0.5 M) generated to elute proteins of interest. A pH gradient, pH 7.5–8.2 was simultaneously applied to improve resolution and to optimize use of anion exchange chromatography. Fractions eluted from the Mono-S cation exchanger were assayed for activity and stored at −80° C. until further use.

4) Superose 12 Gel Filtration

Figure 3:
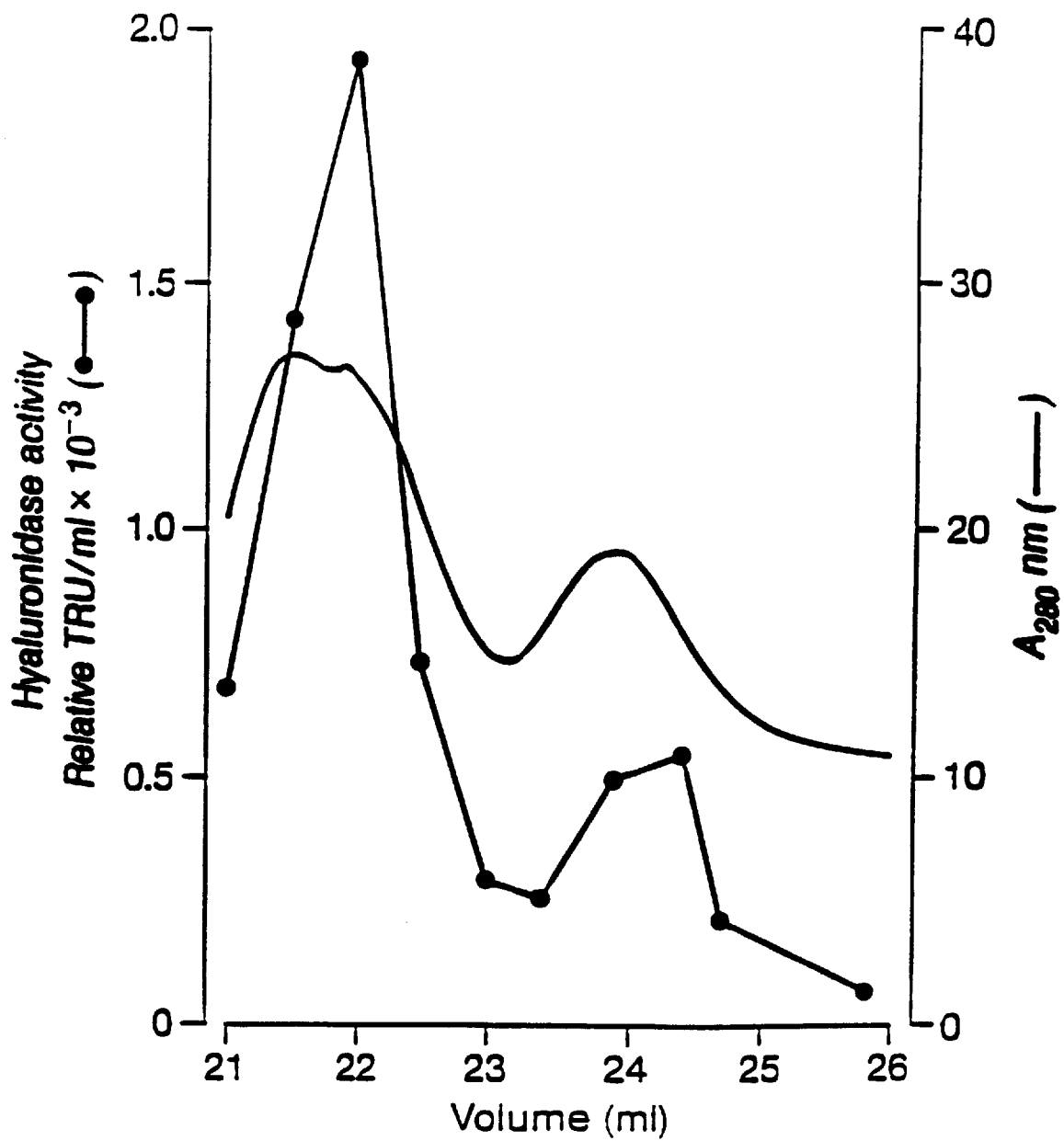
FIG. 3 is a graph showing the elution profile of hyaluronidases on Superose-12 gel filtration chromatography. Closed circles indicate the hyaluronidase activity of each fraction tested. The plain line (no circles) indicates protein concentration.

Active fractions from cation exchange chromatography were concentrated and applied in a 100 μl volume to two Superose-12 FPLC columns linked in series, each equilibrated with 50 mM Hepes, pH 7.5, 0.2 M NaCl, 0.05% Tween 20, at a flow rate of 0.25 ml/min. 200 μl fractions were collected after the void volume and assayed for activity. The gel filtration elution profile of the sample is shown in FIG. 3. The line with closed circles indicates the hyaluronidase activity of each fraction tested, while the plain line (no circles) indicates the protein concentration. Two peaks, peaks A and B, were identified. Peak A is associated with the volumes eluted from the column at 21 ml to 23 ml total eluant. Peak B is associated with volumes eluted from the column at 24 ml to 25 ml total eluant. These peaks presumably represent two separate enzymes.

Table 1 shows the overall purification scheme used to isolate the two enzyme activities contained in the bovine testicular extract, as well as the total activity, specific activity, and percent yield of protein at each step of the purification process.

TABLE 1

Overall Purification Scheme and Activity of Fractions Isolated

| Purification Step | Total Activity (Relative TRU × $10^3$) | Specific Activity (Relative TRU × $10^3$/mg protein) | Yield (%) |
| --- | --- | --- | --- |
| Commercial preparation (Sigma) | 145.9 | 8.9 | 100 |
| Concanavalin-A | 78.8 | 13.2 | 54 |
| Mono-S | 50.1 | 73.8 | 34 |
| Superose-12 (peak A) | 16.6 | 103.8 | 11.4 |
| Superose-12 (peak B) | 4.2 | 71.6 | 2.8 |

EXAMPLE 2
Characterization of BH55 Hyaluronidase by SDS-PAGE Electrophoresis

A 4 μl sample of each of the following were analyzed by SDS-PAGE electrophoresis: 1) the pooled fractions correlating with the hyaluronidase-containing activity from the Concanavalin-A chromatography; 2) the pooled fractions representing the peak of hyaluronidase activity identified during Mono-S chromatography; and 3) the pooled fractions corresponding to the hyaluronidase activity associated with peak B identified by gel filtration. Low molecular weight standards were included as controls. Sodium dodecyl sulfate (SDS) was added to each sample to a concentration of 2.5%, and the samples were electrophoresed through a 12.5% precast polyacrylamide gel with a Pharmacia Phast Gel system (Biorad). The gels were stained with the Phast Gel silver stain kit in a Pharmacia Development unit.

Numerous proteins were apparent in the sample taken from the Concanavalin-A hyaluronidase peak activity, with a few prominent protein bands. SDS-PAGE analysis of the Mono-S hyaluronidase activity peak revealed two proteins corresponding to approximately 75 kDa and 55 kDa each, and a third minor band of higher molecular weight. The protein of approximately 75 kDa is the hyaluronidase PH20. In contrast, the fraction corresponding to peak B identified by gel filtration contained a single protein of approximately 55 kDa. Peak B was tentatively termed BH55 hyaluronidase.

Further SDS-PAGE analysis of the protein isolated in peak B revealed that BH55 hyaluronidase exhibits varying relative molecular masses depending on such variables as concentration of the protein in the source from which it was isolated and the use of reducing or non-reducing conditions in gel electrophoresis analysis. For example, a 14 kDa monomeric protein having characteristics similar to those of BH55 hyaluronidase, including hyaluronidase activity, can be isolated from urine. Upon concentration of urine and SDS-PAGE analysis, the urine hyaluronidase exhibited several different molecular masses that increased in approximately 14 kDa increments. Therefore, without being held to theory, BH55 hyaluronidase may also exist as a complex of 14 kDa monomers. These 14 kDa monomers may associate in various forms including a 40–42 kDa trimer and a 55 kDa tetramer. A BH55 hyaluronidase of greater than 70 kDa has not been observed.

EXAMPLE 3
Analysis of BH55 by Substrate Gel Zymography

The proteins identified by SDS-PAGE analysis were correlated with hyaluronidase activity by zymographic analysis using methods known in the art (Guntenhoener et al., 1992, *Matrix* 12:388–396), with slight modification. Briefly, 0.05–0.5 relative TRU of the activity peak from Mono-S chromatography, peak A from gel filtration, and peak B from gel filtration were suspended in a 2% SDS sample buffer. The samples were applied to non-reducing 10% resolving and 4% stacking polyacrylamide gels, containing 0.1% SDS and 17 μg/ml human umbilical cord hyaluronic acid (ICN Biomedicals). Prestained molecular weight markers (Biorad) were included as a control. Samples were electrophoresed for approximately 45 min. at 20 mA per gel. Following electrophoresis, SDS was substituted by 2.5% Triton-X 100 in a 50 mM Tris buffer, pH 7.6 for 60 min. at 23° C. Gels were then incubated overnight at 37° C. in enzyme assay buffer (0.2 M Formate, pH 4.5, 1 mM sachharolactone). The gels were stained with 0.5% Alcian Blue, 3% acetic acid for 1 hour at 37° C. The gels were then destained exhaustively with 7% acetic acid followed by staining for 45 min with 0.1% Coomassie Blue R250, 40% methanol, 3% acetic acid. The gels were finally destained with 50% methanol, 7% acetic acid and fixed in 5% methanol, 7% acetic acid. Hyaluronidase activity appeared as a clearing against a blue background.

The sample taken from the active fraction from Mono-S chromatography produced a large clear zone at bands corresponding to approximately 75 kDa and 55 kDa molecular weight. The sample from peak A produced a clear zone in the substrate gel at 75 kDa with no other clear zones apparent in the same lane. Likewise, the sample from peak B produced a clear zone at approximately 55 kDa, with no other clear zones apparent in the same lane. These data further confirm that bovine testicular extracts contain two hyaluronidase enzymes. The hyaluronidase activity associated with peak A is PH20 hyaluronidase, while the hyaluronidase activity associated with peak B is BH55, the hyaluronidase of the invention. These two hyaluronidases are distinctly different enzymes and produce distinctly different peaks of hyaluronidase activity.

EXAMPLE 4
Immunoblot Analysis of BH55 Hyaluronidase

Two samples of the proteins corresponding to the Mono-S peak of hyaluronidase activity were subjected to electrophoresis as described above for SDS-PAGE analysis. The proteins were transferred to a PROBLOT® polyvinyl difluoride (PVDF) membrane (Applied Biosystems, Foster City, Calif.) through a semi-dry electrophoretic transfer at 20 mA per gel in the presence of 0.1% SDS in a CAPS buffer, pH 11. The PVDF membrane was blocked with 5% crystalline BSA for one hour on an orbital shaker. The membrane was then cut in half to provide identical membranes, each having one sample of the electrophoresed Mono-S activity peak proteins. The membranes were then incubated with either polyclonal antisera to porcine liver hyaluronidase (Zhu et al., 1994, *J. Biol. Chem.* 269:32092–32097) or recombinant monkey PH-20 (Lin et al., 1993, *Proc. Natl. Acad. Sci. USA* 90:10071–10075; kindly provided by Paul Primakoff) at a 1:200 dilution for 1 hour at 23° C. The membranes were washed with PBS-CMF, 0.1% Tween, and subsequently incubated with a 1:200 dilution of biotinylated anti-rabbit IgG to detect binding of the anti-hyaluronidase antibodies. Antibody binding was visualized through reaction of DAB with the biotin label of the anti-rabbit IgG (avidin-biotin peroxidase kit, Vector Labs, Burlingame Calif.).

Reaction of the anti-PH20 polyclonal antisera with the Mono-S hyaluronidase activity peak detected a single band on the membrane of approximately 75 kDa. In contrast, reaction of the anti-porcine liver hyaluronidase polyclonal antisera with the Mono-S hyaluronidase activity peak detected a single band of approximately 55 kDa. This experiment shows that: 1) BH55 hyaluronidase is not immunologically cross-reactive with monkey PH20; and 2) BH55 hyaluronidase is immunologically cross-reactive with porcine liver hyaluronidase. Furthermore, BH55 hyaluronidase is an enzyme distinct from the PH20 hyaluronidase found in bovine testicular extracts.

EXAMPLE 5
Determination of the N-Terminal Amino Acid Sequence of BH55 Hyaluronidase A sample of the peak activity from the Mono-S chromatography was separated on a 7.5% SDS-PAGE gel and electrophoretically transferred to PVDF membranes as described for above for the immunoblot analysis. The membranes were rinsed with water after blotting and immediately stained with 0.1% Coomassie Blue R250, 40% methanol for one minute followed by destaining in 50% methanol 1% acetic acid. Bands of interest were excised and placed on a solid phase Edman degradation machine for automated protein sequence analysis. The resulting N-terminal amino acid sequence for BH55 hyaluronidase, as well as a comparison of this N-terminal amino acid sequence with that of PH20 hyaluronidase isolated from two different sources, is shown in Table 2. This analysis shows that BH55 hyaluronidase is not PH20 hyaluronidase. Moreover, BH55 hyaluronidase is not closely related to PH20 hyaluronidase since BH55 hyaluronidase does not contain the conserved amino acids APPLIPN (shown in bold) of the PH20 hyaluronidases.

TABLE 2

| N-Terminal Amino Acid Sequence of BH55 Hyaluronidase and Comparison to Known Hyaluronidases | | | | | | | | | | | | |
|---|---|---|---|---|---|---|---|---|---|---|---|---|
| BH55 Hyaluronidase (a superscript | G | P | X | P | I | Y | H | I | Q | E | A | V | L |
| Bovine PH20 (a superscript "b") | S | X | F | X | A | P | P | L | I | P | N | | |
| Guinea pig PH20 (a superscript "c5"). | D | K | F | R | A | P | P | L | I | P | N | | |

EXAMPLE 6
Determination of Amino Acid Sequences of CNBr Fragments of BH55

Cyanogen bromide (CNBr) fragments of BH55 hyaluronidase were generated according to methods well known in the art. Specifically, fractions of BH55 hyaluronidase purified as described above were concentrated using a speed vac and reconstituted in 70% formic acid. A 50 μl portion of this protein solution was mixed with 50 μl of CNBr 120 mg/ml in 70% formic acid and incubated at 23° C. overnight. The reaction was terminated by the addition of 1 ml of distilled water. The material was then concentrated to 10% and reconstituted three times with distilled water. The CNBr-reacted protein was then applied to an Applied Biosystems Pep-HRC column (10 cm). A gradient of 1% acetonitrile/min was then generated between 0.1% TFA in distilled water to 70% acetonitrile, 0.85% TFA in distilled water at a flow rate of 0.2 ml/min. Eluent was analyzed at 215 nm, 254 nm and 280 nm. Homogenous peaks were then analyzed through Edman sequencing on an Applied Biosystems gas phase sequencer.

The CNBr fragments were sequenced by Edman degradation as described above. The sequences of the fragments generated are shown in Table 3.

TABLE 3

Sequences of CNBr Fragments of BH55 Hyaluronidase

| CNBr Fragment No. | Amino Acid Sequence |
| --- | --- |
| 1 | Val—Leu—Xaa—Arg—Glu—Pro—Ala—Gly—Ala—Val—Ile—Xaa—Gly—Tyr—Gly—Thr—Pro—Arg—Ala—Thr—Val—Thr—Val—Thr—Leu—Xaa—Arg (SEQ ID NO: 2) |
| 2 | Gly—Pro—Ser—Ala—His—Ser—Val—Leu (SEQ ID NO: 3) |
| 3 | Met—Lys—Lys—Gly—Thr—Arg—Val—Lys—Xaa—Asp—Ser—Asn (SEQ ID NO: 4) |
| 4 | Lys—Pro—Gly—Gly—Pro (SEQ ID NO: 5) |
| 5 | Xaa—Val—Phe—Gln—Val—Phe—Val—Ala—Xaa—Gly—Glu—Leu (SEQ ID NO: 6) |

*Xaa represent any one of the 20 naturally-occurring amino acids.

EXAMPLE 7
Design of Oligonucleotide Probes-Based Upon Determined Amino Acid Sequences Degenerate oligonucleotides were designed based upon the amino acid sequences of the N-terminal amino acid sequence and the CNBr fragments of BH55 hyaluronidase. The degenerate oligonucleotide probes and the sequences upon which they are based are summarized in Table 4.

mRNA isolation kit. Briefly, bovine testicular tissue frozen in liquid nitrogen is excised and lysed with lysis buffer. Poly-A-containing mRNA is isolated by binding of the poly-A chain to oligo-T DNA bound to cellulose beads. Unbound, non-polyadenylated nucleic acids are removed from the beads by washing, and bound poly-A mRNA is eluted. The isolated mRNA is transcribed into cDNA with reverse transcriptase.

TABLE 4

Degenerate Oligonucleotide Probes for Isolation of DNA encoding BH55 Hyaluronidase

| Amino Acid Sequence Used as Template for Probe Design | Sequence of Degenerate Oligonucleotide Probe |
| --- | --- |
| N-terminal amino acid sequence (SEQ ID NO: 1) | GGCCCCNNNC CCATCTACCA CTACCAGGAG GCCGTGCTG (SEQ ID NO: 9) |
| CNBr fragment #1 (SEQ ID NO: 2) | GUUCUGNNNC GUGAACCGGC UGGUGCUGUU AUCNNNGGUU ACGGUACCCC GCGUGCUACC GUUACCGUUA CCCUGNNNCG U (SEQ ID NO: 10) |
| CNBr fragment #2 (SEQ ID NO: 3) | GGUCCGUCCG CIJCACUCCGU UCUG (SEQ ID NO: 11) |
| CNBr fragment #3 (SEQ ID NO: 4) | AUGAAAAAG GUACCCGUGU UAAANNNGAC UCCAAC (SEQ ID NO: 12) |
| CNBr fragment #4 (SEQ ID NO: 5) | AAACCGGGUG GUCCG (SEQ ID NO: 14) |
| CNBr fragment #5 (SEQ ID NO: x) | NNNGUUUUCC AGGUUUUCGU UGCUNNNGGU GAACUG |

*N may be any of the four naturally-occurring deoxyribonucleotides

The degenerate oligonucleotide probes are synthesized using a DNA synthesizer which is programmed to insert any of the four nucleotides (guanine, adenine, thymine, or cytosine) at the positions indicated by "N" above. Codons used with less than 4% frequency in DNA encoding bovine proteins are not included in the initial primers.

EXAMPLE 8
Cloning of DNA Encoding BH55 Hyaluronidase

Degenerate, synthetic oligonucleotides that include all possible codons for two internal CNBr peptides are synthesized according to methods well known in the art. Codons used with less than 4% frequency in DNA encoding bovine proteins are not included in the initial batch of primers. Both forward and reserve primers are synthesized from each of the two CNBr fragments selected, and are used in separate PCR reactions to establish the order of CNBr fragments.

A bovine testis cDNA library is created according to methods well known in the art, e.g., using an Invitrogene The BH55 gene (or a portion thereof) is amplified from the CDNA library using synthetic degenerate oligonucleotide primers in a 30–35 cycle PCR with Taq polymerase. The amplified DNA fragment is then examined on agarose gel electrophoresis and cloned into a selected plasmid for sequencing using the dideoxy method of Sanger. Once the nucleotide sequence of the amplified fragment of BH55 hyaluronidase is determined, any remaining 5' and/or 3' cDNA is obtained using standard RACE protocols.

EXAMPLE 9
Determination of the DNA Sequence Encoding BH55 Hyaluronidase

The nucleotide sequence of the DNA encoding BH55 hyaluronidase is determined using methods well known in the art, e.g. the dideoxy method of Sanger. The DNA sequence is then compared to the known sequences in the DNA database GenBank to identify any homologous sequences.

EXAMPLE 10
Production of Anti-BH55 Hyaluronidase Antibodies

BH55 hyaluronidase isolated by Superose-12 gel filtration (peak B) is combined with Freund's complete adjuvant and injected into New Zealand albino rabbits. At 21 day intervals, the animals are boosted with protein plus Freund's incomplete adjuvant. After the third boost, serum samples are obtained and antibodies detected using a conventional dot-blot assay. Antibody titers are determined by serial dilutions onto nitrocellulose. Antibody binding is detected using the Problot (Promega) system.

EXAMPLE 11
Expression of BH55 Hyaluronidase Polypeptides

*Escherichia coli* is transformed with a construct containing DNA encoding a BH55 hyaluronidase polypeptide of the invention operably linked to a bacterial promoter. *E. coli* containing the construct are selected by expression of an antibiotic resistance encoded by the construct. The transformed bacterial cells are cultured in a complete bacterial media such as Luria broth under conditions that favor expression of the BH55 hyaluronidase polypeptide-encoding DNA.

After culture, the bacterial cells are separated from the culture by centrifugation and lysed. BH55 hyaluronidase is purified from the bacterial cell lysates using an immunoaffinity column to which an anti-BH55 hyaluronidase antibody is bound. The BH55 hyaluronidase polypeptide is removed from the antibody complexes and refolded as needed to restore activity. The activity of the recombinantly expressed BH55 hyaluronidase is assayed using the ELISA-like hyaluronidase activity assay described above. The purity of the recombinantly expressed BH55 hyaluronidase is assessed by HPLC and/or SDS-PAGE gel electrophoresis.

EXAMPLE 12
Cloning of DNA Encoding Human BH55 Hyaluronidase

The DNA encoding bovine BH55 hyaluronidase is used to generate oligonucleotide probes for the identification of human BH55 hyaluronidase. The oligonucleotide probes are either fragments generated directly from the DNA encoding bovine BH55 hyaluronidase, or are degenerate oligonucleotides whose design is based upon the amino acid sequence of bovine BH55 hyaluronidase. Where degenerate oligonucleotide primers are used, the sequence of these primers takes into account the frequency of codon usage in DNA encoding human proteins. The primers are used in tandem to screen a human cDNA library, preferably a human testis cDNA library according to methods well known in the art. The human BH55 gene (or a portion thereof) is detected after hybridization of the oligonucleotide probe(s) under conditions of high stringency (see, for example, Sambrook et al., supra). Alternatively, the human BH55 hyaluronidase-encoding DNA is amplified from a human cDNA library by PCR according to methods well known in the art (see, for example, Sambrook et al., supra; U.S. Pat. No. 4,800,159). The isolated BH55 hyaluronidase encoding human DNA is then sequenced using the dideoxy method of Sanger, and any remaining 5' and/or 3' DNA is obtained using standard RACE protocol.

Following procedures similar to those described above, other hyaluronidases having substantially the same sequence as BH55 of the invention can be purified, cloned, and expressed.

The invention now being fully described, it will be apparent to one of ordinary skill in the art that many changes and modifications can be made thereto without departing from the spirit or scope of the appended claims.

---

What is claimed is:

1. An isolated DNA molecule encoding bovine BH55 hyaluronidase.

2. An isolated DNA molecule, or degenerate variants thereof, encoding bovine BH55 hyaluronidase.

3. The DNA molecule of claim 1, wherein said DNA molecule is operably linked to regulatory sequences for expression of said BH55 hyaluronidase; and wherein said regulatory sequences comprise a promoter.

4. A vector comprising the DNA molecule of claim 1.

5. A cultured transformed cell which contains the DNA molecule of claim 1.

6. A method of producing a BH55 hyaluronidase comprising:

culturing a cell transformed with a DNA molecule encoding a BH55 hyaluronidase under conditions for expressing said DNA molecule, said DNA molecule being positioned for expression in said cell; and isolating said BH55 hyaluronidase.

7. The DNA molecule of claim 1, wherein the BH55 hyaluronidase comprises the amino acid sequence GPXPIY-HIQEAVL (SEQ ID NO:1).

8. The DNA molecule of claim 1, wherein the BH55 hyaluronidase comprises the amino acid sequences a) Val-Leu-Xaa-Arg-Glu-Pro-Ala-Gly-Ala-Val-Ile-Xaa-Gly-Tyr-Gly-Thr-Pro-Arg-Ala-Thr-Val-Thr-Val-Thr-Leu-Xaa-Arg (SEQ ID NO: 2);

b) Gly-Pro-Ser-Ala-His-Ser-Val-Leu (SEQ ID NO: 3);

c) Met-Lys-Lys-Gly-Thr-Arg-Val-Lys-Xaa-Asp-Ser-Asn (SEQ ID NO: 4);

d) Lys-Pro-Gly-Gly-Pro (SEQ ID NO: 5); and e) Xaa-Val-Phe-Gln-Val-Phe-Val-Ala-Xaa-Gly-Glu-Leu (SEQ ID NO: 6);

where Xaa represents any one of the twenty naturally-occurring amino acids.

\* \* \* \* \*